(12) United States Patent
Johns et al.

(10) Patent No.: US 12,048,567 B2
(45) Date of Patent: *Jul. 30, 2024

(54) SYSTEM, METHOD, AND COMPUTER ALGORITHM FOR MEASURING, DISPLAYING, AND ACCURATELY DETECTING CHANGES IN ELECTROPHYSIOLOGICAL EVOKED POTENTIALS (71) Applicant: SafeOp Surgical, Inc., Hunt Valley, MD (US)

(72) Inventors: Gregg Johns, Hunt Valley, MD (US); Richard O'Brien, Hunt Valley, MD (US); Robert Snow, Hunt Valley, MD (US)

(73) Assignee: SafeOp Surgical, Inc., Carlsbad, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 17/549,764

(22) Filed: Dec. 13, 2021

(65) Prior Publication Data
US 2022/0096022 A1 Mar. 31, 2022

Related U.S. Application Data (63) Continuation of application No. 15/569,367, filed as application No. PCT/US2016/030605 on May 3, 2016, now Pat. No. 11,197,640.
(Continued)

(51) Int. Cl.
A61B 5/00 (2006.01)
A61B 5/24 (2021.01)
(Continued)

(52) U.S. Cl.
CPC ............... *A61B 5/746* (2013.01); *A61B 5/24* (2021.01); *A61B 5/377* (2021.01); *A61B 5/7275* (2013.01); *A61G 13/06* (2013.01); *G16H 50/50* (2018.01)

(58) Field of Classification Search
None
See application file for complete search history.

(56) References Cited

U.S. PATENT DOCUMENTS

| | | | |
|---|---|---|---|
| 4,161,945 A | 7/1979 | Grossman | |
| 4,305,402 A | 12/1981 | Katims | |

(Continued)

FOREIGN PATENT DOCUMENTS

| | | | |
|---|---|---|---|
| CN | 101137332 A | 3/2008 | |
| CN | 101309419 A | 11/2008 | |

(Continued)

OTHER PUBLICATIONS

AMSCO 3085 SP Surgical Table Sales Brochure, STERIS Corporation, Apr. 2006, 16 pages.
(Continued)

*Primary Examiner* — Etsub D Berhanu
(74) *Attorney, Agent, or Firm* — Dentons Durham Jones Pinegar; Sarah W. Matthews (57) ABSTRACT An automated evoked potential analysis apparatus for improved monitoring, detecting and identifying changes to a patient's physiological system is described. The apparatus includes an input device for obtaining electrical potential data from the patient's physiological system after application of stimulation to a patient's nerve and a computing system for receiving and analyzing the electrical potential data. The computing system includes a processing circuit configured to: generate a plurality of evoked potential waveforms (EPs) based on the electrical potential data, measure
(Continued)

changes or trends in the generated EPs utilizing a sliding window of analysis, display incremental changes in waveforms between full subsets of EPs, and determine an alert vote for each subset, representative of changes to the physiological system generating the EPs.

17 Claims, 3 Drawing Sheets

Related U.S. Application Data (60) Provisional application No. 62/156,874, filed on May 4, 2015.

(51) Int. Cl.
*A61B 5/377* (2021.01)
*A61G 13/06* (2006.01)
*G16H 50/50* (2018.01)

(56) References Cited

U.S. PATENT DOCUMENTS

| | | | |
|---|---|---|---|
| 4,863,265 A | 9/1989 | Flower et al. | |
| 4,934,377 A | 6/1990 | Bova et al. | |
| 5,284,154 A | 2/1994 | Raymond et al. | |
| 5,313,956 A | 5/1994 | Knutsson et al. | |
| 5,662,105 A | 9/1997 | Tien | |
| 5,797,854 A | 8/1998 | Hedgecock | |
| 5,825,936 A | 10/1998 | Clarke et al. | |
| 5,827,195 A | 10/1998 | Lander | |
| 5,916,179 A | 6/1999 | Sharrock | |
| 6,067,467 A | 5/2000 | John | |
| 6,304,772 B1 | 10/2001 | Taha et al. | |
| 6,391,024 B1 | 5/2002 | Sun et al. | |
| 6,535,767 B1 | 3/2003 | Kronberg | |
| 6,556,861 B1 | 4/2003 | Prichep | |
| 6,634,043 B2 | 10/2003 | Lamb et al. | |
| 6,725,086 B2 * | 4/2004 | Marinello | A61B 5/1106 600/544 |
| 6,985,833 B2 | 1/2006 | Shambroom et al. | |
| 7,174,206 B2 | 2/2007 | Frei et al. | |
| 7,216,001 B2 | 5/2007 | Hacker et al. | |
| 7,234,180 B2 | 6/2007 | Horton et al. | |
| 7,512,439 B1 | 3/2009 | Farazi | |
| 7,522,953 B2 | 4/2009 | Kaula et al. | |
| 7,620,453 B1 | 11/2009 | Propato et al. | |
| 7,628,757 B1 | 12/2009 | Koh | |
| 7,628,761 B2 | 12/2009 | Gozani et al. | |
| 7,806,862 B2 | 10/2010 | Molnar | |
| 7,904,160 B2 | 3/2011 | Brodnick et al. | |
| 8,055,349 B2 | 11/2011 | Gharib et al. | |
| 8,108,039 B2 | 1/2012 | Saliga et al. | |
| 8,255,045 B2 | 8/2012 | Gharib et al. | |
| 8,386,025 B2 | 2/2013 | Hoppe | |
| 8,515,530 B2 | 8/2013 | Warner et al. | |
| 8,538,512 B1 | 9/2013 | Bibian et al. | |
| 8,538,539 B2 | 9/2013 | Gharib et al. | |
| 8,568,331 B2 | 10/2013 | Bertagnoli et al. | |
| 8,591,431 B2 | 11/2013 | Calancie et al. | |
| 8,731,654 B2 | 5/2014 | Johnson et al. | |
| 8,740,783 B2 | 6/2014 | Gharib et al. | |
| 8,903,487 B1 | 12/2014 | Fischell et al. | |
| 8,965,520 B2 | 2/2015 | Botros et al. | |
| 8,989,866 B2 | 3/2015 | Gharib et al. | |
| 9,084,551 B2 | 7/2015 | Brunnett et al. | |
| 9,211,074 B2 | 12/2015 | Johnson et al. | |
| 9,332,918 B1 | 5/2016 | Buckley et al. | |
| 9,579,037 B2 | 2/2017 | Brunnett et al. | |
| 9,585,618 B2 | 3/2017 | Leschinsky | |
| 9,681,880 B2 | 6/2017 | Neubardt et al. | |
| 9,700,228 B2 | 7/2017 | Gharib et al. | |
| 9,743,853 B2 | 8/2017 | Kelleher | |
| 9,743,884 B2 | 8/2017 | Rasmussen | |
| 9,744,356 B2 | 8/2017 | Botros et al. | |
| 10,342,443 B2 | 7/2019 | Johnson et al. | |
| 10,376,167 B2 | 8/2019 | Mahon et al. | |
| 10,391,012 B2 | 8/2019 | Stashuk et al. | |
| 11,083,387 B2 | 8/2021 | Mahon et al. | |
| 11,197,640 B2 | 12/2021 | Johns et al. | |
| 11,684,533 B2 | 6/2023 | Stashuk et al. | |
| 2002/0042563 A1 | 4/2002 | Becerra et al. | |
| 2002/0183605 A1 | 12/2002 | Devlin et al. | |
| 2003/0052775 A1 | 3/2003 | Shambroom et al. | |
| 2003/0083719 A1 | 5/2003 | Shankar et al. | |
| 2003/0125777 A1 | 7/2003 | Ding et al. | |
| 2003/0176799 A1 | 9/2003 | Beatty et al. | |
| 2004/0010303 A1 | 1/2004 | Bolea | |
| 2004/0122482 A1 | 6/2004 | Tung et al. | |
| 2005/0075578 A1 | 4/2005 | Gharib et al. | |
| 2005/0085866 A1 | 4/2005 | Tehrani | |
| 2005/0101878 A1 | 5/2005 | Daly et al. | |
| 2005/0119711 A1 | 6/2005 | Cho et al. | |
| 2005/0228306 A1 | 10/2005 | Kurtz | |
| 2005/0228654 A1 | 10/2005 | Prieto et al. | |
| 2005/0261559 A1 | 11/2005 | Mumford et al. | |
| 2006/0025702 A1 | 2/2006 | Sterrantino et al. | |
| 2006/0052845 A1 | 3/2006 | Zanella | |
| 2006/0173510 A1 | 8/2006 | Besio et al. | |
| 2006/0178593 A1 | 8/2006 | Neubardt et al. | |
| 2006/0241562 A1 | 10/2006 | John et al. | |
| 2006/0276704 A1 | 12/2006 | McGinnis et al. | |
| 2007/0016097 A1 | 1/2007 | Farquhar et al. | |
| 2007/0135722 A1 | 6/2007 | Lin | |
| 2007/0192960 A1 | 8/2007 | Jackson | |
| 2007/0225674 A1 | 9/2007 | Molnar et al. | |
| 2007/0282217 A1 | 12/2007 | Mcginnis et al. | |
| 2008/0033511 A1 | 2/2008 | Dobak | |
| 2008/0051844 A1 | 2/2008 | Brodnick et al. | |
| 2008/0167574 A1 | 7/2008 | Farquhar | |
| 2008/0221473 A1 | 9/2008 | Calancie et al. | |
| 2008/0269835 A1 | 10/2008 | Carlson et al. | |
| 2008/0300655 A1 | 12/2008 | Cholette | |
| 2009/0033486 A1 | 2/2009 | Costantino | |
| 2009/0048531 A1 | 2/2009 | McGinnis et al. | |
| 2009/0054758 A1 | 2/2009 | Dunseath | |
| 2009/0054804 A1 | 2/2009 | Gharib et al. | |
| 2009/0069027 A1 | 3/2009 | Brock et al. | |
| 2009/0124869 A1 | 5/2009 | Hu et al. | |
| 2009/0143693 A1 | 6/2009 | Ye et al. | |
| 2009/0177112 A1 | 7/2009 | Calancie et al. | |
| 2009/0247893 A1 | 10/2009 | Lapinlampi et al. | |
| 2010/0010367 A1 | 1/2010 | Foley et al. | |
| 2010/0036211 A1 | 2/2010 | La Rue et al. | |
| 2010/0042012 A1 | 2/2010 | Alhussiny | |
| 2010/0130834 A1 | 5/2010 | Vertio-Oja et al. | |
| 2010/0144200 A1 | 6/2010 | Holliday | |
| 2010/0156376 A1 | 6/2010 | Fu et al. | |
| 2010/0198099 A1 | 8/2010 | Murphy et al. | |
| 2010/0274144 A1 | 10/2010 | Hu et al. | |
| 2010/0312124 A1 | 12/2010 | Johnson et al. | |
| 2010/0317989 A1 | 12/2010 | Gharib et al. | |
| 2011/0054346 A1 | 3/2011 | Hausman et al. | |
| 2011/0224570 A1 | 9/2011 | Causevic | |
| 2011/0224988 A1 | 9/2011 | Mahajan et al. | |
| 2011/0230785 A1 | 9/2011 | Higgins et al. | |
| 2011/0279676 A1 | 11/2011 | Terada et al. | |
| 2011/0295142 A1 | 12/2011 | Chakravarthy et al. | |
| 2012/0065536 A1 | 3/2012 | Causevic et al. | |
| 2012/0095360 A1 | 4/2012 | Runney et al. | |
| 2012/0136276 A1 | 5/2012 | Johnson et al. | |
| 2012/0150063 A1 | 6/2012 | Rea | |
| 2012/0165690 A1 | 6/2012 | Chen et al. | |
| 2012/0197153 A1 | 8/2012 | Kraus et al. | |
| 2012/0313757 A1 | 12/2012 | Volpi et al. | |
| 2013/0024524 A1 | 1/2013 | Graff et al. | |
| 2013/0035606 A1 | 2/2013 | Wichner | |
| 2013/0190599 A1 | 7/2013 | Wyeth et al. | |
| 2013/0204156 A1 | 8/2013 | Hampton et al. | |
| 2013/0245424 A1 | 9/2013 | Decharms | |
| 2013/0245722 A1 | 9/2013 | Ternes et al. | |
| 2014/0020178 A1 * | 1/2014 | Stashuk | A61B 5/383 600/554 |

(56) References Cited

U.S. PATENT DOCUMENTS

| | | |
|---|---|---|
| 2014/0121555 A1 | 5/2014 | Scott et al. |
| 2014/0148725 A1 | 5/2014 | Cadwell |
| 2014/0275926 A1 | 9/2014 | Scott |
| 2014/0276195 A1 | 9/2014 | Papay et al. |
| 2014/0288389 A1 | 9/2014 | Gharib et al. |
| 2014/0324118 A1 | 10/2014 | Simon et al. |
| 2015/0061758 A1 | 3/2015 | Hsu |
| 2015/0088030 A1 | 3/2015 | Taylor |
| 2015/0148683 A1 | 5/2015 | Hermanne |
| 2015/0208934 A1 | 7/2015 | Sztrubel et al. |
| 2015/0257700 A1 | 9/2015 | Fu |
| 2015/0313512 A1 | 11/2015 | Hausman et al. |
| 2016/0106994 A1 | 4/2016 | Crosby et al. |
| 2016/0113587 A1 | 4/2016 | Kothe et al. |
| 2016/0128620 A1 | 5/2016 | Iriki et al. |
| 2016/0213268 A1 | 7/2016 | Kim et al. |
| 2016/0228018 A1 | 8/2016 | Mahon et al. |
| 2016/0270679 A1 | 9/2016 | Mahon et al. |
| 2017/0347955 A1 | 12/2017 | Rasmussen |
| 2018/0078210 A1 | 3/2018 | Snow et al. |
| 2018/0078220 A1 | 3/2018 | Johns et al. |
| 2018/0140843 A1 | 5/2018 | Kent et al. |
| 2018/0310849 A1 | 11/2018 | Johns et al. |
| 2018/0360336 A1 | 12/2018 | O'Brien et al. |
| 2020/0315478 A1 | 10/2020 | Mahon et al. |
| 2022/0096022 A1 | 3/2022 | Johns et al. |
| 2022/0287619 A1 | 9/2022 | Cleveland et al. |

FOREIGN PATENT DOCUMENTS

| | | |
|---|---|---|
| CN | 201185940 Y | 1/2009 |
| CN | 102481107 A | 5/2012 |
| CN | 104411234 A | 3/2015 |
| JP | 20090118969 A | 6/2009 |
| JP | 2012529344 A | 11/2012 |
| WO | 2001074248 A1 | 10/2001 |
| WO | 2003000128 A2 | 1/2003 |
| WO | 2003005887 A2 | 1/2003 |
| WO | 2006072050 A2 | 7/2006 |
| WO | 2006084193 A2 | 8/2006 |
| WO | 2010144200 A1 | 12/2010 |
| WO | 2011045936 A1 | 4/2011 |
| WO | 2013166157 A1 | 11/2013 |
| WO | 2015048822 A1 | 5/2015 |
| WO | 2016179191 A1 | 11/2016 |
| WO | 2018232365 A1 | 12/2018 |
| WO | 2022192569 A1 | 9/2022 |

OTHER PUBLICATIONS

Warner et al. (Dec. 1994) "Ulnar Neuropathy. Incidence, Outcome, and Risk Factors in Sedated or Anesthetized Patients" Anesthesiology, 81(6):1332-1340.

Winfree et al. (Jan. 2005) "Intraoperative Positioning Nerve Injuries" Surgical Neurology, 63(1):5-18.

IOM and Neurophysiological Monitoring Software, NeuroStream, Apr. 21, 2010, 1 page.

Intraoperative Monitoring Document Management, NeuroStream, Apr. 21, 2010, 1 page.

Intraoperative Monitoring Interpreting Physician Access, NeuroStream, Apr. 21, 2010, 1 page.

Software for Intraoperative Monitoring Scheduling, NeuroStream, Apr. 21, 2010, 1 page.

Baumann et al. (Jan. 2000) "Intraoperative SSEP Detection of Ulnar Nerve Compression or Ischemia in an Obese Patient: A Unique Complication Associated with a Specialized Spinal Retraction System" Archives of Physical Medicine and Rehabilitation, 81(1):130-132.

Ben-David et al. (Oct. 1997) "Prognosis of Intraoperative Brachial Plexus Injury: A Review of 22 Cases" British Journal of Anaesthesia, 79(4):440-445.

Bizzarri et al. (Jan. 2001) "Iatrogenic Injury to the Long Thoracic Nerve", Texas Heart Institute Journal, 28(4):315-317.

Chung et al. (Apr. 2009) "Upper-limb somatosensory evoked potential monitoring in lumbosacral spine surgery: a prognostic marker for position-related ulnar nerve injury" The spine journal: official journal of the North American Spine Society, 9(4):287-295.

Fishel et al. (Jun. 1990) "Postoperative Injuries of Upper Limb Nerves" The Clinical Journal of Pain, 6(2):128-130.

Graham et al. (Jul. 1981) "Brachial Plexus Injury After Median Sternotomy" Journal of Neurology, Neurosurgery, and Psychiatry, 44(7):621-625.

Hickey et al. (Jan. 1993) "Intraoperative Somatosensory Evoked Potential Monitoring Predicts Peripheral Nerve Injury During Cardiac Surgery" Anesthesiology, 78(1):29-35.

Jellish et al. (Feb. 1997) "Hands-up Positioning During Asymmetric Sternal Retraction for Internal Mammary Artery Harvest: A Possible Method to Reduce Brachial Plexus Injury" Anesthesia & Analgesia, 84(2):260-265.

Kamel et al. (May 2006) "The Use of Somatosensory Evoked Potentials to Determine the Relationship Between Patient Positioning and Impending Upper Extremity Nerve Injury During Spine Surgery: A Retrospective Analysis" Anesthesia & Analgesia, 102(5):1538-1542.

Labrom et al. (Sep. 15, 2005) "Clinical Usefulness of Somatosensory Evoked Potentials for Detection of Brachial Plexopathy Secondary to Malpositioning in Scoliosis Surgery" Spine, 30(18):2089-293.

Makarov et al. (Mar.-Apr. 1996) "Intraoperative SSEP Monitoring During External Fixation Procedures in the Lower Extremities" Journal of Pediatric Orthopaedics, 16(2):155-160 (1-8 pages).

Makarov et al. (Sep.-Oct. 1997) "Monitoring Peripheral Nerve Function During External Fixation of Upper Extremities" Journal of Pediatric Orthopaedics, 17(5):663-667 (1-8 pages).

Nagda et al. (May-Jun. 2007) "Neer Award 2005: Peripheral Nerve Function During Shoulder Arthroplasty Using Intraoperative Nerve Monitoring" Journal of Shoulder and Elbow Surgery, 16(3 Suppl):7 pages.

Posta et al. (Dec. 1997) "Neurologic Injury in the Upper Extremity After Total Hip Arthroplasty" Clinical Orthopaedics and Related Research, 345:181-186.

Prielipp et al. (Aug. 1999) "Ulnar Nerve Pressure: Influence of Arm Position and Relationship to Somatosensory Evoked Potentials" Anesthesiology, 91(2):345-354.

Crum, et al. " Peripheral nerve stimulation and monitoring during operative procedures." Muscles & nerve 35.2: 159-170. (Year: 2007).

Crum, et al. "intraoperative peripheral nerve stimulation and recording." Handbook of Clinical Neurophysiology 8: 364-370. (Year: 2008).

Doemges, et al., "Changes in the Stretch Reflex of the Human First Dorsal Interosseous Muscle During Different Tasks," Journal of Physiology, 1992, pp. 563-573, vol. 447.

European Patent Office acting as International Searching Authority, " Search Report and Written Opinion," International Application No. PCT/US2022/019798, Jul. 6, 2022.

European Patent Office, "Communication Pursuant to Article 94(3) EPC," European Application No. 18771706.1, mailed Jul. 4, 2023.

European Patent Office, "Extended European Search Report," European Application No. 23188630.0, Sep. 5, 2023.

Hongxuan Zhang et al., "Intraoperative Neurological Monitoring," vol. 25, No. 4, Jul. 1, 2006 (Jul. 1, 2006), pp. 39-45.

International Search Report and Written Opinion for PCT Application No. PCT/US2010/034076, dated Jul. 9, 2010, 8 pages.

International Search Report and Written Opinion, PCT/US16/30605, dated Aug. 8, 2016.

Japan Patent Office, "Office Action," Japanese Application No. 2022191709, mailed Nov. 14, 2023.

Makeig, et al., Mining event-related brain dynamics, Trends in Cognitive Sciences. vol. 8, No. 5, May 2004, pp. 204-210.

Extended European Search Report issued in European Application No. 16789949.1, mailed on Dec. 4, 2018, 7 pages.

Extended European Search Report issued in European Application No. 13784125.0, mailed on Dec. 9, 2015, 8 pages.

(56) References Cited

OTHER PUBLICATIONS

International Search Report and Written Opinion received for PCT Application No. PCT/US2016/030605, mailed on Aug. 8, 2016, 8 pages.
International Search Authority, "Search Report and Written Opinion," International Application No. PCT/US/2023/029024, Dec. 15, 2023.

\* cited by examiner

SYSTEM, METHOD, AND COMPUTER ALGORITHM FOR MEASURING, DISPLAYING, AND ACCURATELY DETECTING CHANGES IN ELECTROPHYSIOLOGICAL EVOKED POTENTIALS

RELATED APPLICATIONS

This application is a continuation of U.S. application Ser. No. 15/569,367, filed Oct. 25, 2017, and entitled "SYSTEM, METHOD, AND COMPUTER ALGORITHM FOR MEASURING, DISPLAYING, AND ACCURATELY DETECTING CHANGES IN ELECTROPHYSIOLOGICAL EVOKED POTENTIALS," which is a national stage entry of International Application No. PCT/US2016/030605, filed May 3, 2016, and entitled "SYSTEM, METHOD, AND COMPUTER ALGORITHM FOR MEASURING, DISPLAYING, AND ACCURATELY DETECTING CHANGES IN ELECTROPHYSIOLOGICAL EVOKED POTENTIALS," which claims priority from Provisional Application U.S. Application 62/156,874, filed May 4, 2015, entitled "SYSTEM, METHOD, AND COMPUTER ALGORITHM FOR MEASURING, DISPLAYING, AND ACCURATELY DETECTING CHANGES IN ELECTROPHYSIOLOGICAL EVOKED POTENTIALS," each of which is incorporated herein by reference in its entirety. This application is also related to U.S. patent application Ser. No. 13/874,867 (published as U.S. Patent Publication 2014/0020178), filed May 1, 2013, entitled "SYSTEM, METHOD, AND COMPUTER ALGORITHM AND CHARACTERIZATION AND CLASSIFICATION OF ELECTROPHYSIOLOGICAL EVOKED POTENTIALS," which is hereby incorporated by reference in its entirety.

BACKGROUND

The present invention relates generally to computer programs and methods for detecting changes in evoked potential (EP) waveforms, and more particularly to systems, methods, and computer-readable medium, which use a mathematical algorithm to assess and display EP waveforms, and calculate alerts to waveform changes.
Standard Attended Intraoperative Monitoring Somatosensory evoked potentials are summated electrical potentials usually recorded from the head or neck area and a peripheral nerve after repeatedly stimulating a peripheral nerve. Monitoring patients using somatosensory evoked potentials during surgery has been shown to allow early identification of impending injury, particularly nerve injury.

Such monitoring generally requires highly trained technologists under physician supervision with sophisticated, multichannel amplifier and display equipment. Unfortunately, such personnel and equipment are limited in their availability, require pre-booking, and are costly. In addition, such monitoring is fraught with difficulties due to the small size of potentials and ongoing noise which make recognizing significant changes, and alerting of these changes, difficult. In current systems that are used to generate alerts automatically, substantial noise and variability can cause false alerts.

Embodiments described herein relate to improved, systems, methods and devices for accurately detecting changes in electrophysiological evoked potentials. Improvements to existing systems include reduction in false positive/false negative alerts due to signal noise. Accordingly, the improved systems, methods, and devices generate more accurate alerts. Reducing the number of false positive alerts also creates more efficient systems, methods, and devices compared to known systems.

SUMMARY OF THE INVENTION

Embodiments described herein relate to methods, devices, systems, apparatuses, and/or means to automatically detect and display changes to the evoked potential waveforms (EPs) in real time while showing incremental changes between completed ensemble averages. Embodiments described herein also relate to producing alerts with reduced or eliminated influence of variable noise and bias, while minimizing or eliminating false negative and false positive errors. The present disclosure generally relates to the computer signal processing and display algorithms for the characterization and classification of changes to EPs in real-time. The disclosed embodiments can be used in lieu of expert analysis typically provided by the technologist and physician. Further, various embodiments can be used in conjunction with other equipment. For example, upon detecting a change in EPs, an operating room table can be moved or adjusted. Such movement allows the patient to be automatically moved to ameliorate or avoid patient injury. Thus various embodiments herein extend the benefit of such equipment by automatically controlling the equipment based upon the EPs.

When seeking to accurately monitor or detect somatosensory evoked potentials (SSEPs), the waveforms can require acquisition at specific frequencies and/or averaging together to help eliminate random and cyclical noise. Even a few aberrant waveforms heavily affected by noise can markedly change the apparent amplitude (height) or latency (time of onset) of a waveform of interest when averaged together. While this is partly avoided by careful choice of stimulation frequencies and filtering of the waveforms, such methods cannot be complete as the waveforms of interest fall within the frequency range of the background noise and the cyclical background noise varies somewhat in frequency. In addition, these methods require producing a complete average (Ensemble Average or EA) of 100-300 stimulations and resultant waveforms, and then confirming any suspected change based on comparison with another EA, each taking up to 3 minutes to collect.

There is presently no way of observing slow onset incremental changes or discounting aberrant epochs affected by noise. The cost of having professionals fully engaged in interpreting these waveforms results in limiting of the service to only the most high risk surgeries. In addition, interpretation may be biased by human factors such as prior negative patient outcomes.

Thus, embodiments herein generally relate to systems, methods, devices and computer algorithms for measuring, displaying, and accurately detecting changes in electrophysiological evoked potentials. In some aspects the embodiments can automatically detect and display changes to the EPs in real time, including while showing incremental changes between completed ensemble averages. Also, in some aspects the embodiments can provide alerts free of the influence of variable noise and bias, including while minimizing or eliminating false negative and false positive errors. Embodiments described herein generally relate to the computer signal processing and display algorithms for the characterization and classification of changes to EPs in real-time implemented on specialized devices and systems.

This systems and devices utilizing the algorithms may substitute for the expert analysis typically provided by the technologist and physician.

In an exemplary embodiment of the present invention a system, method, and computer algorithm for measuring, displaying and accurately detecting changes in electrophysiological evoked potentials is disclosed. In this disclosure, an EP is defined as a voltage versus time signal obtained by ensemble averaging of the electrophysiological responses to repetitive stimulation of a specific neural system, detected using suitable electrodes. Examples of EPs are somatosensory, auditory or visual EPs. The algorithms are applied to a time sequence of EPs acquired over the course of an ongoing clinical procedure. The algorithms establish changes to the characteristics of an EP relative to the baseline/normal EP, as well as to any previous EPs to determine if the functioning of the underlying neural system has been significantly affected by the ongoing clinical procedure. The algorithms communicate with ancillary hardware and algorithms developed to acquire the sequence of EPs and provide suitable feedback to ensure a safe and effective clinical workflow. The algorithms provide the basis for a clinically effective application such that false positives and false negatives are minimized.

Further features and advantages of the invention, as well as the structure and operation of various embodiments of the invention, are described in detail below with reference to the accompanying drawings.

BRIEF DESCRIPTION OF DRAWINGS

The foregoing and other features and advantages of the invention will be apparent from the following, more particular description of a preferred embodiment of the invention, as illustrated in the accompanying drawings.

DETAILED DESCRIPTION

Various exemplary embodiments of the invention including preferred embodiments are discussed in detail below. While specific exemplary embodiments are discussed, it should be understood that this is done for illustration purposes only. A person skilled in the relevant art will recognize that other components and configurations can be used without parting from the spirit and scope of the invention.

Figure 1:
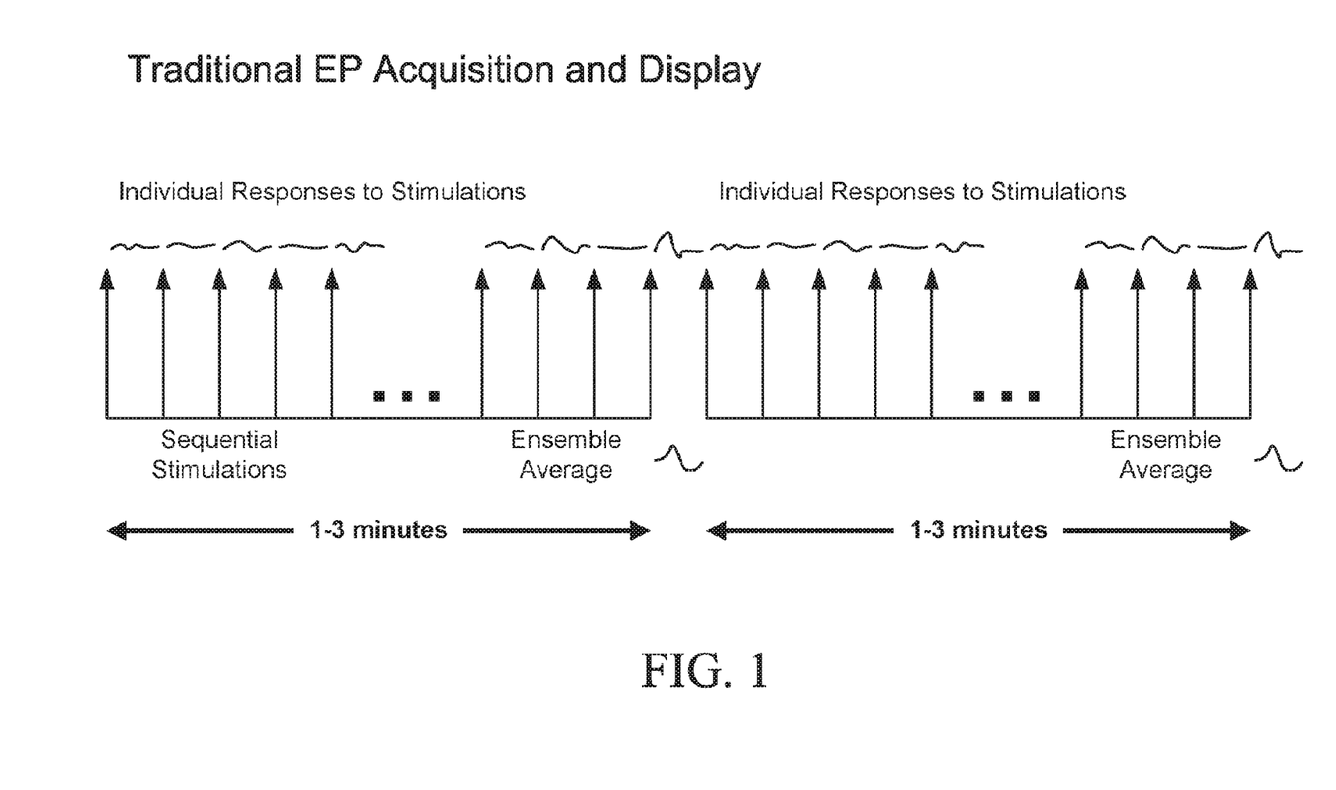
FIG. 1 illustrates the traditional method evoked potential waveform (EP) acquisition and display.

FIG. 1. illustrates a traditional way in which EPs are acquired and displayed. Using this method, a series of stimulations are applied and the resultant individual waveforms are displayed either as each is acquired, or as an evolving average of the ongoing average until a final ensemble average is acquired and displayed. The clinical interpretation is based on this ensemble average. If the user is satisfied with the average they may set that average as the 'baseline' to which all others are compared, or repeat it to confirm the presence and morphology of the waveform of interest. The whole process is then repeated with the next series of stimulations. Comparison of that series is then made to the preceding one that is chosen to be the baseline.

Since as few as five or six noisy individual waveforms that escape filtering can cause the waveform morphology, amplitude, and latency to widely vary, applying this method in an electrically noisy environment may lead to erroneous alerting of potential, imminent injury if an automated alerting system is used. This generally requires expert interpretation of the individual waveforms that takes into account the clinical situation, expected waveform and general trend in the waveform pattern over time.

An embodiment of the present invention relates to the computer signal processing and algorithms for the display of EP waveforms, calculation of alerts to waveform changes, and minimization of false positive and false negative alerts. This algorithm may substitute for the expert analysis typically provided by the technologist and physician. The computer algorithm running in software installed on an EP machine may be used in any surgery or situation where a patient is at risk, in order to detect, alert, and ameliorate positioning effect, or any nerve injury or abnormality.

Figure 2:
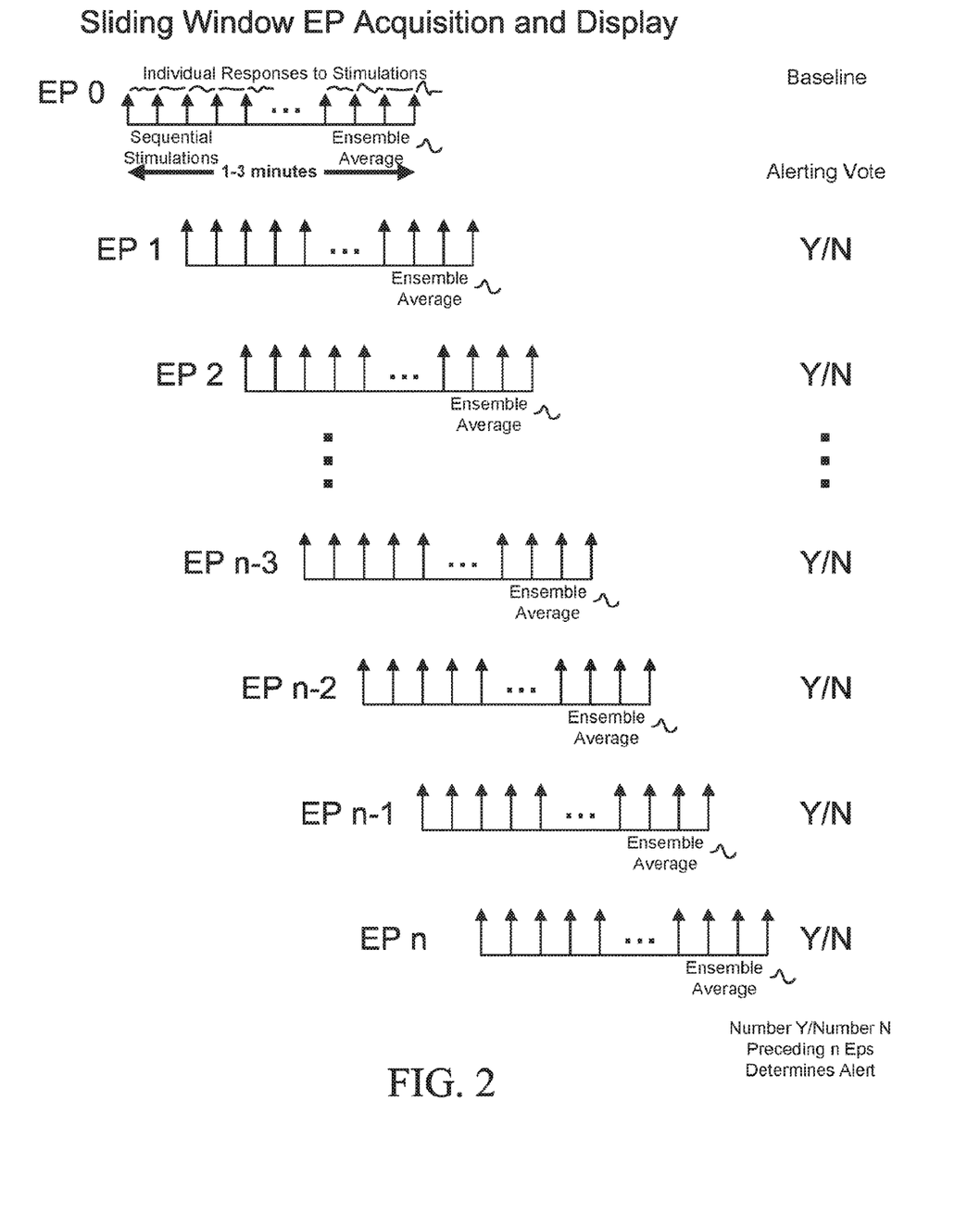
FIG. 2 illustrates a sliding window method of EP acquisition, display, and alerting, according to an exemplary embodiment of the present invention.

FIG. 2. illustrates an exemplary depiction of a sliding window of analysis and alerting using metadata from automatically calculated alerts that takes into consideration variation in noise and automatically looks back at the trend of the waveform over time, according to the present invention.

After collection of one or more sets of EPs, an Ensemble Average (EA) is created and a baseline of the waveform of interest is calculated. The baseline waveform may be identified by any standard technique including for example wavelet analysis, curve fitting etc.

For the next "n" number of stimulations, a new EA is created using similar waveforms as the previous one but from which a number of EPs are removed from the beginning of the average and a similar number is added to the end. For example, as shown on FIG. 2, EP2 does not incorporate the first two EPs of EP1, and includes two additional EPs at the end. Thus achieving a "sliding window" selection of EP data on which to create the new EA for the ongoing stimulation series. In certain preferred embodiments, a new EA is created for every epoch, i.e. the "window" slides forward only one EP, eliminating the first and adding an additional one to the end, relative to the previous EP selection for the previous EA.

The overall average can be updated and displayed with every overlapping epoch allowing a slow change in the morphology to evolve for the viewer. In this way, the viewer observes a real-time, incremented change in the EP waveform morphology over time, similar to viewing a live event or motion picture. In an exemplary embodiment of the invention, the generated overlapping EAs allows display of the effect of incremental consequence on the baseline average caused by newly collected waveforms in between non-overlapping EAs.

Each new EA waveform is identified and the salient characteristic (for example amplitude or latency) is measured and recorded. The new values are compared to the baseline value of the characteristic and it is determined whether an alert vote is to be generated. An alert vote is generated if the characteristic reaches a change threshold, i.e., a degree of change the user has set to trigger an alert. This process is repeated. Each new EA generates a vote as to whether an alert should be triggered or not. When the number of EAs reaches a specific number (n), typically when the initial stimuli of the EA no longer overlap the baseline EA, the votes are tallied and, in preferred embodiments, only then can an alert be triggered depending upon the ratio of yes to no (Y/N) alert votes required to trigger an alert. The user may alter the ratio of alert votes (Y/N) required depending upon their wish for specificity of the alerting process. In other embodiments, the votes may be continuously tallied and an alert triggered once the yes (Y) votes reach a certain predetermined number, or the ratio reaches a predetermined value.

In an exemplary embodiment of the invention, since the voting process may be asymmetrical, different ratios of voting may be used for triggering (onset) and releasing (offset) a final alert to the user that nerve injury to the patient is possible or imminent.

The alerting process examines the meta-data (the alerting vote) for the individual overlapping epochs. Since any real change in data will be sustained and always eventually deliver 100% (or close) Y/N votes for alert, the specificity of the alerting process can now be manipulated independent of the sensitivity of the system on the basis of the voting. For example, the user may alter the ratio to be less specific, requiring only 30% or 50% of votes vs 80% of votes for more specificity. In this way, there can be a reduction in the number of false alerts without really altering the sensitivity of the process to detecting real sustained change. In currently used systems, substantial noise and variability can cause false alerts, whereas the voting ratio used according to the present invention lessens the impact of the noisy signals. In an exemplary embodiment of the invention, EAs with wildly variant waveform values can be discarded from the voting process, eliminating intermittent noise that escapes the frequency filters. Thus, embodiments have an improved way of handling the effects of noise in EPs. The effect of this noise is further nullified by the voting process itself Going forward the process is repeated, the voting using the last 'n' number of EAs to decide if an alert is triggered and displaying each EA or an averaged group of EAs as a progressively changing waveform which can easily be compared to baseline visually. In various embodiments, when an alert is triggered other actions can also occur. For example, information leading to the alert trigger can be sent to other equipment. As another example, a command to move a portion of an operating room table can be sent to the operating room table. Upon receipt, the operating room table can move and thus move the position of the patient. The movement reduces the patient's risk of nerve injury.

In an exemplary embodiment of the invention, once the process is established, a smooth ongoing generation of overlapping EAs can identify gradual changes that are due to processes such as cooling or depth of anesthesia that are not due to more abrupt onset injuries.

Figure 3:
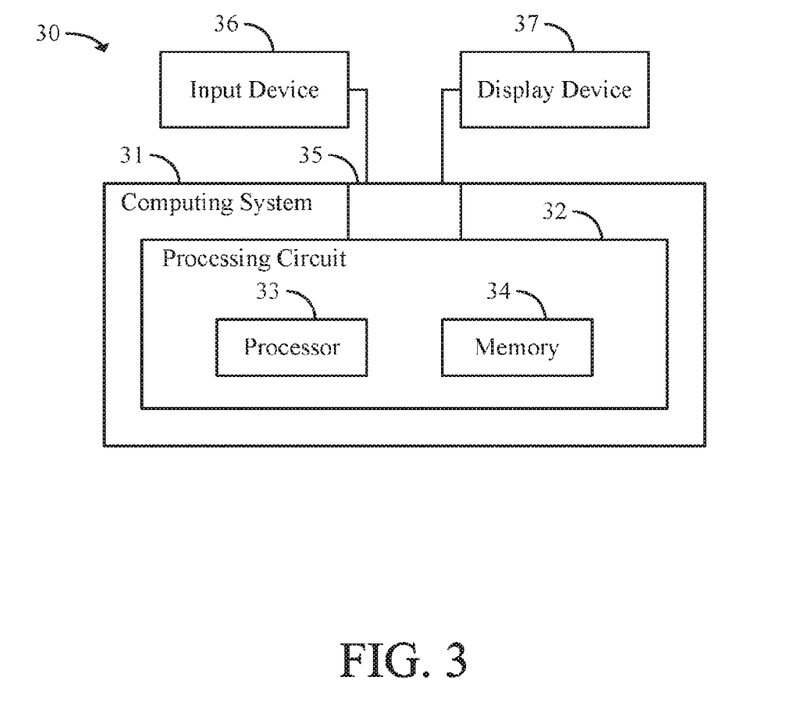
FIG. 3 is a block diagram of a model EP analysis apparatus according to an exemplary embodiment.

Referring to FIG. 3, according to an exemplary embodiment, the EP analysis described above is implemented with an EP analysis apparatus 30. The EP analysis apparatus 30 includes hardware and software for operation and control of the system. According to an exemplary embodiment, the EP analysis apparatus 30 includes a computing system 31, an input device 36, and a display device 37. The computing system comprises a processing circuit 32 having a processor 33 and memory 34. Processor 33 can be implemented as a general purpose processor, an application specific integrated circuit (ASIC), one or more field programmable gate arrays (FPGAs), a group of processing components, or other suitable electronic processing components. Memory 34 (e.g., memory, memory unit, storage device, etc.) is one or more devices (e.g., RAM, ROM, Flash-memory, hard disk storage, etc.) for storing data and/or computer code for completing or facilitating the various processes described in the present application. Memory 34 may be or include volatile memory or non-volatile memory. Memory 34 may include database components, object code components, script components, or any other type of information structure for supporting the various activities described in the present application. According to an exemplary embodiment, memory 34 is communicably connected to processor 33 and includes computer code for executing one or more processes described herein. The memory 34 may contain a variety of modules, each capable of storing data and/or computer code related to specific types of functions.

Referring still to FIG. 3, the computing system 31 further includes a communication interface 35. The communication interface 35 can be or include wired or wireless interfaces (e.g., jacks, antennas, transmitters, receivers, transceivers, wire terminals, etc.) for conducting data communications with external sources via a direct connection or a network connection (e.g., an Internet connection, a LAN, WAN, or WLAN connection, etc.).

What is claimed is:

1. An automated evoked potential analysis apparatus for monitoring, detecting, and identifying changes to a patient's physiological system, wherein the apparatus comprises:
   an input device for obtaining electrical potential data from the patient's physiological system after application of stimulation to a nerve of the patient;
   a computing system for receiving and analyzing the electrical potential data, and comprising a processing circuit configured to:
   generate a series of evoked potential waveforms (EPs) based on the electrical potential data;
   calculate a series of ensemble average waveforms (EAs) as the EPs are generated where each EA represents a subset of the plurality of EPs with each new EA including the most recent EP while omitting at least the earliest EP contained in the immediately preceding EA;
   identify a characteristic in each EA;
   determine an alert vote for each subset, representative of changes to the physiological system generating the EPs, the determining the alert vote comprising:
   creating a positive alert vote if the characteristic of a particular EA reaches a change threshold compared to the characteristic of a preceding EA; and
   creating a negative alert vote if the characteristic of the particular EA does not reach the change threshold compared to the preceding EA;
   determine, after calculating at least one subsequent EA that does not overlap with at least one preceding EA, whether a ratio of positive alert votes to negative alert votes exceeds a threshold value; and
   trigger, upon determining that the ratio exceeds the threshold value, an alert.

2. The apparatus of claim 1, wherein each EA contains the same number of EPs.

3. The apparatus of claim 1, wherein the processing circuit is further configured to display each calculated EA so as to display incremental changes between each sequential subset of EPs.

4. The apparatus of claim 1, wherein said apparatus is further configured to integrate into other devices in a surgical environment.

5. The apparatus of claim 4, wherein said computing system is further configured to feed information to other devices in the surgical environment that allows these devices to manually or automatically ameliorate or mitigate the physiological changes and improve subsequently acquired EP waveforms.

6. The apparatus of claim 5, further comprising an operating table, wherein the operating table is configured to be adjustable to ameliorate or mitigate the physiological changes by causing an adjustment of the patient's position, in response to the information from the computing system.

7. The apparatus of claim 1, wherein said apparatus computing system is further configured to identify gradual changes that are due to cooling or depth of anesthesia.

8. The apparatus of claim 1, wherein the characteristic in each EA comprises a latency, an amplitude, or a morphology.

9. The apparatus of claim 1, wherein said apparatus computing system is further configured to identify gradual changes that are due to cooling of the patient.

10. A method of automatically identifying potential injury to peripheral nerve structures, the method comprising:
   stimulating, by an output device of an automated evoked potential analysis apparatus, a peripheral nerve with electrical pulses;
   recording, by an input device of the automated evoked potential analysis apparatus, resultant electrical waveforms (EPs) generated by the nervous system, wherein the input device comprises electrodes placed over a nerve pathway;
   measuring, by a computing system of the automated evoked potential analysis apparatus, changes in acquired EPs utilizing a sliding window of analysis, the computing system comprising a processing circuit, wherein utilizing the sliding window of analysis comprises:
      calculating, by the computing system, a series of ensemble average waveforms (EAs), each EA comprising a subset of the plurality of EPs with each new EA including the latest EP while excluding at least the earliest EP contained in the last EA, displaying, by the computing system, a second EA to display incremental changes between a first and a second subset of EPs; and
      identifying, by the computing system, a characteristic in each EA;
   determining, by the computing system, an alert vote for each subset, representative of changes to the physiological system generating the EPs, the determining the alert vote comprising:
      creating, by the computing system, a positive alert vote if the characteristic of a particular EA reaches a change threshold compared to the characteristic of a preceding EA; and
      creating, by the computing system, a negative alert vote if the characteristic of the particular EA does not reach the change threshold compared to the preceding EA;
   determining, by the computing system and after calculating at least one EA that does not overlap with at least one preceding EA, whether a ratio of positive alert votes to negative alert votes exceeds a threshold value;
   triggering, by the computing system, upon determining that the ratio exceeds the threshold value, an alert; and
   alerting, by the computing system, a user to the changes.

11. The method of claim 10, wherein the sliding window analysis further comprises displaying, by the computing system, each EA so as to display incremental changes between each subsequent subset of EPs.

12. The method of claim 10, wherein the characteristic in each EA comprises a latency, an amplitude, or a morphology.

13. The method of claim 10, further comprising passing, by the computing system, information related to alerts to an automated operating room table and readjusting patient position through adjustment of the table.

14. The method of claim 13, wherein adjustment of the operating room table is performed, by the computing system, automatically or semi automatically.

15. The method of claim 10, further comprising passing, by the computing system, information related to alerts to other devices or processes.

16. The method of claim 10, wherein the electrodes are placed at the neck or head of a patient.

17. The method of claim 10, wherein the method further comprises identifying gradual changes that are due to cooling or depth of anesthesia.

* * * * *